United States Patent

Boussignac et al.

[11] Patent Number: 6,102,041
[45] Date of Patent: Aug. 15, 2000

[54] RESPIRATORY ASSISTANCE DEVICE

[76] Inventors: Georges Boussignac, 1, avenue de Provence; Jean-Claude Labrune, 2, avenue de Guyenne, both of 92160 Antony, France

[21] Appl. No.: 08/156,679

[22] Filed: Nov. 22, 1993

Related U.S. Application Data

[63] Continuation of application No. 08/156,679, Nov. 22, 1993, abandoned, which is a continuation of application No. 07/963,002, Oct. 19, 1992, abandoned, which is a continuation of application No. 07/750,232, Aug. 20, 1991, abandoned, which is a continuation of application No. 07/419,690, Oct. 11, 1989, abandoned.

[30] Foreign Application Priority Data

Oct. 26, 1988 [FR] France .................. 88 13978

[51] Int. Cl.⁷ .................................................. A61M 16/00
[52] U.S. Cl. ........................................ 128/207.15; 128/912
[58] Field of Search ........................ 128/200.24, 200.26, 128/207.14–207.16, 911, 912, 204.25

[56] References Cited

U.S. PATENT DOCUMENTS

| | | | |
|---|---|---|---|
| 3,794,026 | 2/1974 | Jacobs | 128/202.22 |
| 3,881,479 | 5/1975 | Carden | 128/207.15 |
| 4,265,237 | 5/1981 | Schwanbom et al. | 128/204.25 |
| 4,270,530 | 6/1981 | Baum et al. | 128/207.15 |
| 4,285,340 | 8/1981 | Gezari et al. | 128/205.24 |
| 4,289,128 | 9/1981 | Rüsch | 128/207.15 |
| 4,471,775 | 9/1984 | Clair et al. | 128/207.15 |
| 4,519,388 | 5/1985 | Schwanbom et al. | 128/207.15 |
| 4,573,462 | 3/1986 | Baum | 128/207.15 |
| 4,584,998 | 4/1986 | McGrail | 128/207.15 |
| 4,617,015 | 10/1986 | Joltz | 128/207.15 |
| 4,630,606 | 12/1986 | Weerda et al. | 128/207.14 |
| 4,632,108 | 12/1986 | Geil | 128/207.15 |
| 4,633,864 | 1/1987 | Walsh | 128/207.15 |
| 4,739,756 | 4/1988 | Horn | 128/207.15 |
| 4,813,431 | 3/1989 | Brown | 128/207.15 |
| 4,898,168 | 2/1990 | Yule | 128/207.15 |

FOREIGN PATENT DOCUMENTS

| | | |
|---|---|---|
| 0074809 | 3/1983 | European Pat. Off. . |
| 0245142 | 11/1987 | European Pat. Off. . |
| 3327342 | 2/1985 | Germany . |
| 2114896 | 9/1983 | United Kingdom . |

*Primary Examiner*—Aaron J. Lewis
*Attorney, Agent, or Firm*—Marshall, O'Toole, Gerstein, Murray & Borun

[57] ABSTRACT

A respiratory assistance device comprises a respiratory aid tube whose distal extremity, intended to be introduced into the windpipe of a patient, is provided with an inflatable ballonet and means for bringing the respiratory gas into the lungs of the patient by means of said tube. The device includes pressure sensors in the ballonet and at the distal end of the tube which provide signals to an electronic controller for controlling the feed of respiratory gas to the patient.

14 Claims, 2 Drawing Sheets

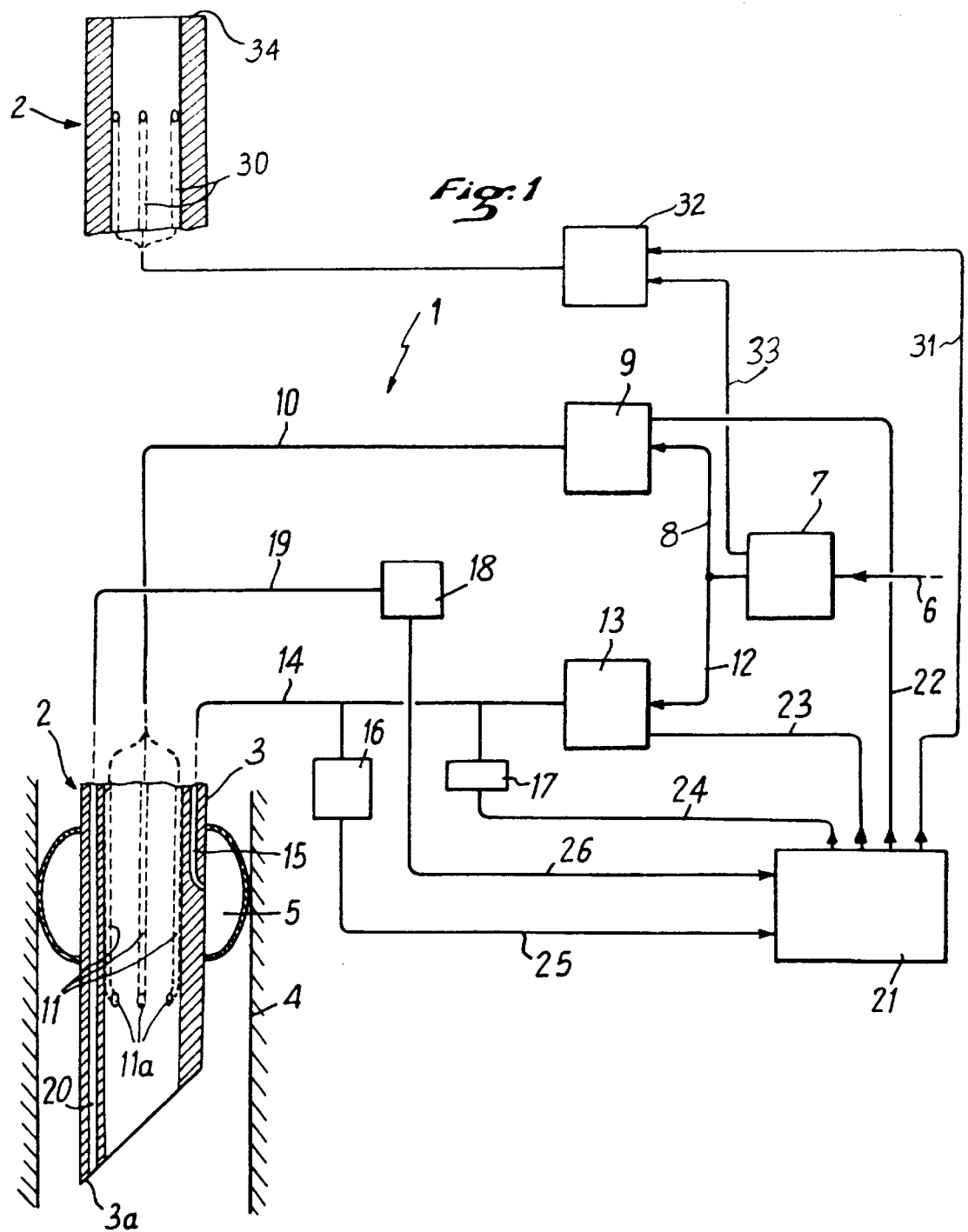

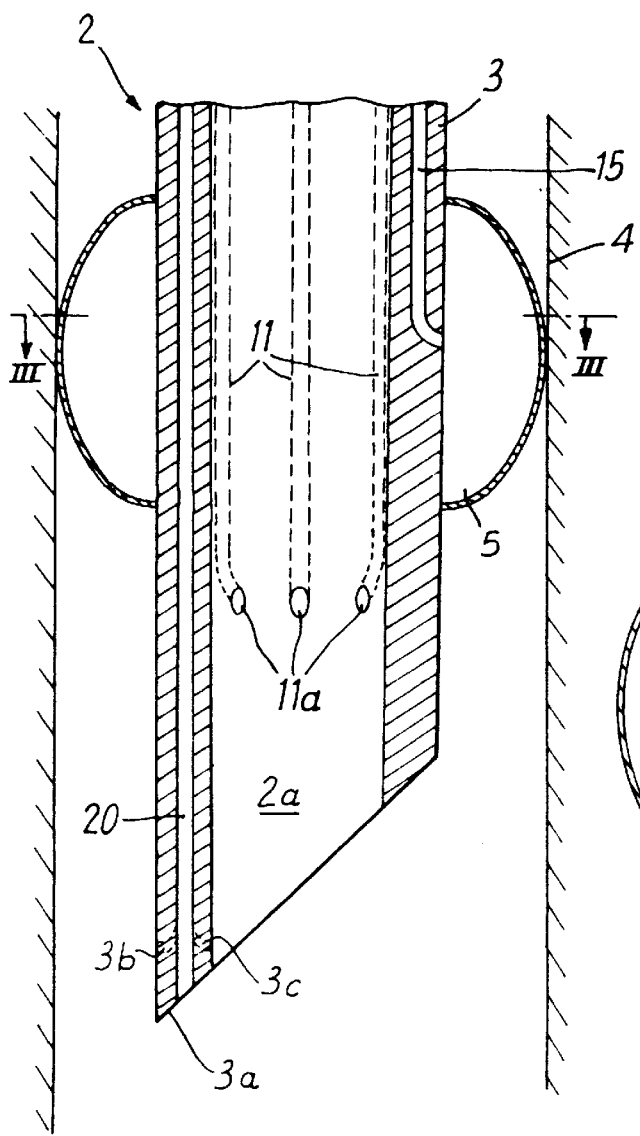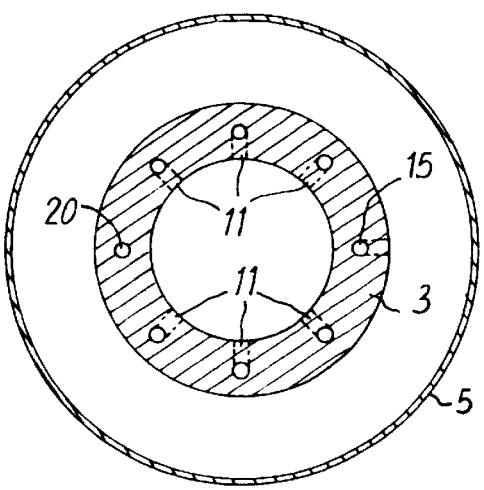

RESPIRATORY ASSISTANCE DEVICE

This is a continuation of U.S. Ser. No. 08/156,679 filed Nov. 22, 1993, now abandoned, which is a continuation of U.S. Ser. No. 07/963,002 filed Oct. 19, 1992, now abandoned, which is a continuation of U.S. Ser. No. 07/750,232 filed Aug. 20, 1991, now abandoned, which is a continuation of U.S. Ser. No. 07/419,690 filed Oct. 11, 1989, now abandoned.

FIELD OF THE INVENTION

The object of the present invention is to provide a respiratory assistance device able to be used on patients whose spontaneous breathing is absent or inadequate.

BACKGROUND OF THE INVENTION

There are already known to exist respiratory assistance devices comprising means to bring the respiratory gas into the lungs of a patient, and to possibly remove said gas from these lungs, by means of a respiratory assistance tube whose distal extremity is generally intended to be introduced into the windpipe of the patient. In this case, it is normal practice to dispose an inflatable ballonet at the distal extremity of the probe. Accordingly, there is a risk of excess pressure occurring in the lungs of the patient if feeding of the gas is not strictly controlled, this excess pressure frequently proving to be dangerous for the patient.

SUMMARY OF THE INVENTION

The object of the invention is to overcome this drawback and concerns a respiratory assistance device of the type indicated above whereby any risk of excess pressure occuring in the lungs can be avoided.

To this effect, the respiratory assistance device of the invention, said device comprising a respiratory assistance tube, whose distal extremity, intended to be introduced into the windpipe of a patient, is provided with an inflatable ballonet, and means to feed the respiratory gas into the lungs of the patient by means of said tube, is notable in that it includes first means for detecting variations of the pressure inside said ballonet.

Thus, any excess pressure inside the ballonet indicates an excess pressure, or at least a risk of excess pressure, in the lungs, thus making it possible to adjust feeding the patient with the respiratory gas. Furthermore, the detection of pressure variations in the ballonet makes it possible to avoid any risk of excess pressure occuring inside said ballonet, which as a result could damage the wall of the windpipe on which said ballonet rests.

According to another characteristic of the invention, the device includes second means for detecting the pressure downstream of said ballonet. Thus, it is possible to detect the "real" pressure existing inside the lungs.

Advantageously, said first detection means are constituted by a pressure sensor connected to the gas feeding pipe of the ballonet.

In particular, a safety valve can be connected to said ballonet gas feeding pipe. Thus, if required, it is possible to quickly deflate the ballonet.

In addition, said second detection means may be constituted by a pressure sensor connected to said pipe opening downstream of said ballonet at the distal extremity of said tube.

According to a further characteristic of the invention, the distal extremity part of the tube comprises a first capillary housed inside the wall of said tube and connected to said first detection means and opening into said ballonet.

Advantageously, the distal extremity part of the tube comprises a second capillary housed inside the wall of said tube and connected to said second detection means and opening downstream of the ballonet.

Furthermore, the distal extremity part of the tube may comprise a plurality of capillaries housed inside the wall of said tube for feeding respiratory gas to the patient. Preferably, the extremity opening into said tube of each of said gas-feeding capillaries is preshaped. The preshaping of these capillaries consists of a preshaping whose shape is similar to the general shape, as well as the section variations, of a Venturi tube. This specific preshaping allows for optimization of the dynamic performances of respiratory fluids concerning a continuous adjustment of flows, the quality of mixtures and insufflation pressures with respect to pulmonary elasticity.

In addition, the device may include suitably-adapted electronics so as to control feeding of the patient with the respiratory gas and inflation of said ballonet according to the information transmitted by said first and second pressure detection means.

BRIEF DESCRIPTION OF THE DRAWINGS

The figures of the annexed drawing shall clearly explain how the invention is able to be embodied.

FIG. 1 is a synoptic diagram of the respiratory assistance device of the invention.

FIG. 2 is a longitudinal section of the distal extremity part of the intubation probe.

FIG. 3 is a section along the line III—III of FIG. 2.

DETAILED DESCRIPTION OF THE PREFERRED EMBODIMENTS

With reference in particular to FIG. 1, the respiratory assistance device 1 includes a respiratory assistance tube 2 whose distal extremity 3, intended to be introduced into the windpipe 4 of a patient, is provided with an inflatable ballonet 5. The purpose of this ballonet 5 is to keep the extremity 3 of the tube in position in the windpipe 4 and to avoid any uncontrolled "return" of the respiratory gas through the windpipe.

In addition, an intake 6 for supplying respiratory gas under pressure, said gas possibly being oxygen or a gas mixture containing oxygen, is connected to a pressure regulator 7 delivering an output pressure of, for example, 3 bars. The pressure regulator 7 is also connected via a pipe 8 to means 9 for controlling feeding the patient with the respiratory gas. These control means may be constituted by electrovalves controlling the insufflatory and possibly expiratory respiratory assistance periods of the patient. Moreover, the control means 9 are connected via a pipe 10 to a plurality of capillaries 11 housed in the wall of the distal extremity part 3 of the tube 2 so as to provide the patient with the respiratory gas and whose extremity 11a opening into the tube is preshaped.

Furthermore, the pressure regulator 7 is connected via a pipe 12 to means 13 for controlling inflation of the ballonet 5, said means also being connected via a pipe 14 to a capillary 15 housed inside the wall of the distal extremity part 3 of the tube and opening into the ballonet 5.

A pressure sensor 16 detects the pressure in pipe 14 which feeds gas to ballonet 5, while a safety valve 17 prevents the development of pressure in pipe 14 above a controllable maximum value. A pressure sensor 18 is also provided and is connected via a pipe 19 to a capillary 20 housed inside the wall of the distal extremity part 3 of the tube opening downstream of the ballonet 5 and preferably, as shown on the drawing, to the point 3a of the extremity 3 of the tube 2. The capillary 20 could also open at 3b or 3c for obvious safety reasons so as to avoid any obstructions possibly caused by serious fluids originating from the respiratory device.

The respiratory assistance device 1 further includes suitably-adapted electronics 21 so as to control the respiratory gas-feeding of the patient (link 22) and the inflation (and possibly the draining) of the ballonet 5 (links 23 and 24) according to the information transmitted by the pressure sensors 16 and 18 by means of the links 25 and 26 respectively.

The respiratory assistance device 1 may also include an automatic control system required to feed the capillaries 30 with gas so as to provoke expiratory assistance. The electronics 21 are adapted so as to control the gas-feeding (link 31) of the capillaries 30 through a control device 32 receiving the gas from the pressure regulator 7 and a feed pipe 33. The capillaries 30 are housed in the wall of the proximal extremity 34 of the tube 2 and make it possible to embody a drive of the gases exhaled by the patient according to the principles of fluid mechanics. As for the capillaries 11, the extremities of the capillaries 30 and of the wall of the tube 2 are configured according to "Venturi" type section variations so as to obtain the sought-after flow quality.

The respiratory device 1 could thus have available a complete respiratory cycle automatic control system controlled by the pressure sensors 16 and 18. The device shall accordingly be a device provided with electronics making it possible to successively time-adjust the period of inspiration and the period of expiration whilst observing the idle times desired and adjusted by the operator. Pressure control shall make it possible to easily maintain a positive pressure by means of a continuous feeding on a capillary 11 and even at the end of the expiration cycle. The respiratory device could also be provided with other adjustment probes, a hygrometry measuring probe or a flow measuring probe.

The respiratory assistance device of the invention thus makes it possible to provide a patient with the respiratory gas without the risk of excess pressure occuring in the patient's lungs due to the fact that the pressure in the ballonet 5 representative of the pressure in the lungs and the "real" pressure can be measured by the respective pressure sensors 16 and 18 and, on the basis of these measurements, it is possible to adjust the respiratory gas-feeding of the patient, as well as inflation of the ballonet.

As used herein and in the appended claims, the terms "upstream" and "downstream" relate to the direction of flow of inhaled respiratory gas from the respiratory device of the invention into the lungs of a patient.

What is claimed is:

1. A respiratory assistance device, comprising:

a respiratory assistance tube adapted to be introduced into the windpipe of a patient;

an inflatable ballonet coupled to said respiratory assistance tube;

a first pipe fluidly coupled to an interior portion of said inflatable ballonet, said first pipe being coupled to a source of gas, said first pipe allowing said inflatable ballonet to be inflated with gas;

a first pressure sensor, said first pressure sensor generating a signal representative of a gas pressure within said inflatable ballonet;

a second pipe associated with said respiratory assistance tube, said second pipe being in fluid communication with the windpipe of the patient at a point downstream of said inflatable ballonet when said respiratory assistance tube is disposed in the windpipe of the patient;

a second pressure sensor, said second pressure sensor being in fluid communication with said second pipe, said second pressure sensor generating a signal representative of a gas pressure within the windpipe of the patient at a point downstream of said inflatable ballonet when said respiratory assistance tube is disposed in the windpipe of the patient; and an electronic control circuit that controls a cyclic flow of respiratory gas supplied to the patient through said respiratory assistance tube, said electronic control circuit adjusting the respiratory gas provided to the patient based upon said signals generated by said first and second pressure sensors, said adjustment of the respiratory gas being done while said inflatable ballonet is inflated and sealed against an interior portion of the windpipe of the patient to avoid uncontrolled return of the respiratory gas through the windpipe of the patient.

2. A respiratory assistance device as defined in claim 1 wherein said first pipe comprises a gas passageway formed in a portion of said respiratory assistance tube.

3. A respiratory assistance device as defined in claim 1 wherein said second pipe comprises a gas passageway formed in a portion of said respiratory assistance tube.

4. A respiratory assistance device as defied in claim 1 additionally comprising a safety valve associated with said first pipe to allow escape of gas from said inflatable ballonet.

5. A respiratory assistance device as defined in claim 1 wherein a plurality of respiratory gas passageways are formed in said respiratory assistance tube.

6. A respiratory assistance device as defined in claim 1 additionally comprising a pressure regulator and a gas feed control device, said gas feed control device being operatively coupled to said electronic control circuit.

7. A respiratory assistance device as defined in claim 1 additionally comprising a pressure control device that controls the gas pressure within said ballonet.

8. A respiratory assistance device, comprising:

a respiratory assistance tube adapted to be introduced into the windpipe of a patient;

an inflatable ballonet coupled to said respiratory assistance tube;

a first pipe fluidly coupled to an interior portion of said inflatable ballonet, said first pipe being coupled to a source of gas, said first pipe allowing said inflatable ballonet to be inflated with gas;

a first pressure sensor, said first pressure sensor generating a signal representative of a gas pressure within said inflatable ballonet;

a second pipe associated with said respiratory assistance tube, said second pipe being in fluid communication with the windpipe of the patient at a point downstream of said inflatable ballonet when said respiratory assistance tube is disposed in the windpipe of the patient;

a second pressure sensor, said second pressure sensor being in fluid communication with said second pipe, said second pressure sensor generating a signal representative of a gas pressure within the windpipe of the patient at a point downstream of said inflatable ballonet when said respiratory assistance tube is disposed in the windpipe of the patient; and an electronic control circuit that controls inflation of said ballonet based upon said signals generated by said first and second pressure sensors.

9. A respiratory assistance device as defined in claim 8 wherein said first pipe comprises a gas passageway formed in a portion of said respiratory assistance tube.

10. A respiratory assistance device as defined in claim 8 wherein said second pipe comprises a gas passageway formed in a portion of said respiratory assistance tube.

11. A respiratory assistance device as defined in claim 8 additionally comprising a safety valve associated with said first pipe to allow escape of gas from said inflatable ballonet.

12. A respiratory assistance device as defined in claim 8 wherein a plurality of respiratory gas passageways are formed in said respiratory assistance tube.

13. A respiratory assistance device as defined in claim 8 additionally comprising a pressure regulator and a gas feed control device, said gas feed control device being operatively coupled to said electronic control circuit.

14. A respiratory assistance device as defined in claim 8 additionally comprising a pressure control device that controls the gas pressure within said ballonet.

* * * * *